United States Patent [19]

Chasalow et al.

[11] Patent Number: 5,130,256
[45] Date of Patent: Jul. 14, 1992

[54] DIAGNOSTIC ASSAY FOR BREAST CANCER IN HUMAN FEMALE PATIENTS

[75] Inventors: Fred I. Chasalow, Glen Cove; H. Leon Bradlow, Holliswood, both of N.Y.

[73] Assignee: Long Island Jewish Medical Center, New Hyde Park, N.Y.

[21] Appl. No.: 752,188

[22] Filed: Aug. 23, 1991

Related U.S. Application Data

[63] Continuation of Ser. No. 278,829, Dec. 2, 1988, abandoned.

[51] Int. Cl.$^5$ ............................................. G01N 33/48
[52] U.S. Cl. .................................. 436/64; 436/63; 436/813; 436/169; 422/70; 210/635; 210/656
[58] Field of Search .................... 436/63, 64, 813, 169; 422/70; 210/635, 656

[56] References Cited

U.S. PATENT DOCUMENTS 4,440,863  4/1984  Haagensen ........................ 436/539

OTHER PUBLICATIONS

Raju et al., "Correlation of Concentrations of Estriol-3-Sulfate With Those of Potassium and Sodium in Human Breast Cyst Fluid", *Steroids* 45(3-4) pp. 341-346 (1985).

Raju et al., "Estriol Conjugates in Human Breast Cyst Fluid and in Serum of Premenopausal Women", J. of Clin. Endocrinol. Metab. (45)(3) pp. 429-434 (1977).

Raju et al., "Estriol In Human Breast Cyst Fluid", J. Steroid Biochem. vol. 20, No. 4B pp. 1061-1065 (1984).

Raju et al. "Androsterone Long Chain Fatty Acid Esters in Human Breast Cyst Fluid", J. Clin. Endocrinol Metab. 60 No. 5 pp. 940-946 (1985).

*Primary Examiner*—Robert J. Warden
*Assistant Examiner*—Lyle A. Alexander
*Attorney, Agent, or Firm*—Darby & Darby

[57] ABSTRACT

A method for determining whether a woman with gross cystic disease will develop breast cancer is provided. The method comprises analyzing human breast cyst fluid for the presence of a unique factor which has a retention time on an Amino Carbohydrate HPLC column of between about 6.4 minutes and about 6.7 minutes. The presence of this factor is diagnostically predictive for breast cancer.

6 Claims, 6 Drawing Sheets

DIAGNOSTIC ASSAY FOR BREAST CANCER IN HUMAN FEMALE PATIENTS

This is a continuation of application Ser. No. 07/278,829, filed Dec. 2, 1988 now abandoned.

BACKGROUND OF THE INVENTION

This invention is related to a diagnostic assay useful for determining which individuals afflicted with gross cystic disease of the breast will develop breast cancer.

Approximately 200,000 women develop breast cancer each year. It is the leading cause of death of women under 40 years of age. Early detection and treatment are the keys to survival from this disease. Mammography and self-examination are important factors in early detection of this disease. However, no independent biological measurements have yet been developed which can be used to determine which individuals will develop breast cancer.

Cystic breast disease is a common condition in premenopausal women, occurring predominantly in women between the ages of 30 and menopause. Patients afflicted with gross cystic disease of the breast have an approximately 2-4 fold increased incidence of breast carcinoma when compared to women without cysts. Approximately 10-20% of those afflicted with gross cystic disease have been found to go on to develop breast cancer.

Fluid derived from the breasts of human females with gross cystic disease contains a broad spectrum of biological molecules. In particular, human breast cyst fluid has been found to contain high concentrations of materials which cross-react with antibodies directed against digoxin in specific radioimmunoassay procedures for this cardiac glycoside. U.S. Pat. application Ser. Nos. 939,552 and 130,805, filed Dec. 9, 1986 and Dec. 9, 1987, respectively both of Fred I. Chasalow and H. Leon Bradlow disclose a biologically active agent isolated from Type 1 human breast cyst fluids which cross reacts with digoxin antibodies and has anti-hypertensive activity in mammals.

U.S. Pat. No. 4,440,863 issued Apr. 3, 1984 of Haagensen, Jr. discloses a glycoprotein isolated from breast cyst fluid and also detected in the serum of breast cancer patients. However, the assay for this glycoprotein was said to be insensitive for detection of early breast carcinoma.

What is needed in the art is a method for determining which of those women afflicted with gross cystic disease are at increased risk for developing breast cancer over and above the risk associated with cystic disease itself.

It is an object of the present invention to provide a method for diagnosing those individuals at increased risk for developing breast cancer.

SUMMARY OF THE INVENTION

The present inventors have unexpectedly discovered a method for determining which patients with gross cystic disease will subsequently develop breast cancer.

One aspect of the present invention provides a method for determining whether a patient afflicted with gross cystic disease will be at increased risk to develop breast cancer, the method comprising the steps of collecting a sample of breast cyst fluid from said patient, extracting said fluid with an organic solvent, fractionating said extracted fluid using High Pressure Liquid Chromatography on an Amino-Carbohydrate column and an acetonitrile gradient, and isolating a fraction from said column having a retention time of between about 6.4 and 6.7 minutes on said column, said fraction comprising a factor absorbing light at 210 nm, and measuring the quantity of said factor present in said fraction.

Another aspect of the present invention provides a purified factor present in human breast cyst fluid having a retention time of between about 6.4 minutes and about 6.7 minutes when chromatographed on High Pressure Liquid Chromatography using an Amino Carbohydrate column with an acetonitrile gradient as a solvent.

These and other aspects of the present invention will be apparent to those of ordinary skill in the art in view of the present specification, accompanying claims and appended drawings.

DETAILED DESCRIPTION OF THE INVENTION

Figure 1:
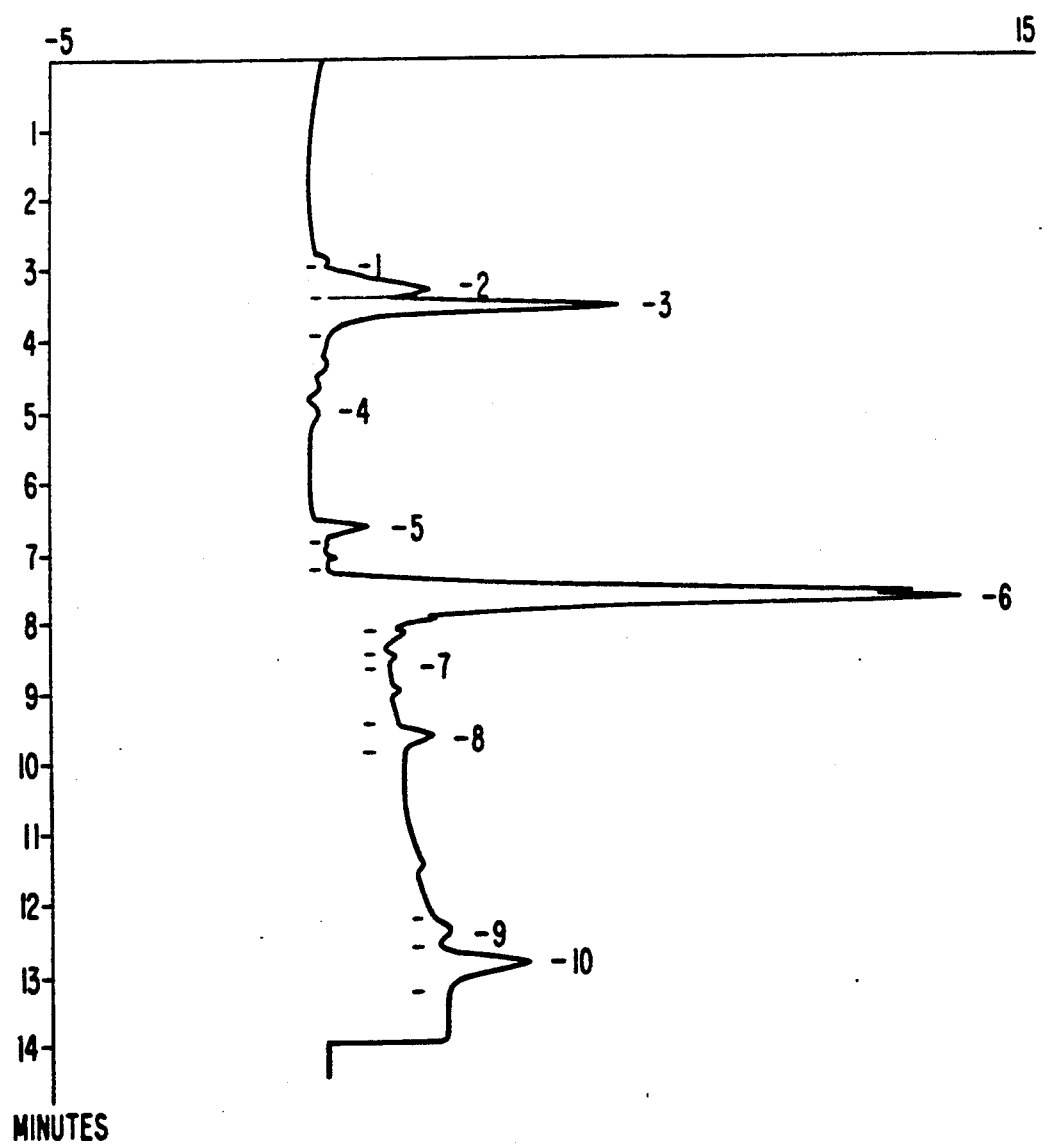
FIG. 1 is an HPLC chromatogram of an extract from Type 1 human breast cyst fluid from an individual without breast cancer.

The present inventors have unexpectedly discovered a method which can be used to identify individuals at increased risk for developing breast cancer. This is a most important finding as early detection of breast cancer is a key for survival. The present invention is based on the unexpected discovery that factors can be isolated from human breast cyst fluids (i.e. Type 1, 2 and A, see below) which, when present, may be used to determine whether a patient with gross cystic disease is at increased risk to develop breast cancer.

Human breast cyst fluid can be categorized into major types based on its electrolyte composition. Type 1 fluids have high $K^+$ concentration and low $Na^+$ and when compared to those present in Type 2 fluids which have low $K^+$ concentration and high $Na^+$ and $Cl^-$ concentration; Type A fluids have levels of $K^+$ and $Na^+$ ions intermediate between those of Type 1 and Type 2 fluids.

The factors of the present invention, present in human breast cyst fluids, can be detected at least 6 months before the clinical diagnosis of breast cancer is made. Therefore, when these factors are present in these fluids, the patient can be very closely monitored in order to detect the first clinical signs of the disease and to institute the requisite therapies.

Based upon its biochemical properties (i.e. absorbance at 210 nm, acetonitrile solubility, retention on an Amino Carbohydrate column), the present inventors believe that the factors of the present invention are aglycones covalently attached to a polysaccharide moiety.

The present inventors initially undertook to measure digoxin-like materials in fluids obtained by fine-needle biopsy from women with fibrocystic disease of the breast. Levels of total materials which cross react with digoxin antibodies were elevated in Type 1 fluids (with high $K^{30}$ ion concentration and low $Na^+$ and $Cl^-$ ion concentrations) when compared to those present in Type 2 fluids (with low $K^{30}$ ion concentration and high $Na^+$ and $Cl^-$ concentration). When analyzed by HPLC, it was found that some women with Type 1 cyst fluid who subsequently were diagnosed as having breast cancer also had a unique material in their cyst fluid. In addition, cyst fluid obtained from some women who subsequently were diagnosed as having breast cancer was found to contain a factor which had a substantially larger UV (at 210 nm) absorbing peak at 7.4 to 7.8 minutes retention time when analyzed by HPLC than that present in control extracts. The presence of this peak (which was greater than 2 standard deviations larger then that found in a control) is also correlated with the development of breast cancer.

The method of the present invention comprises obtaining cyst fluid samples, extracting the cyst fluid with an organic solvent, and chromatographing the extract on High Pressure Liquid Chromatography (HPLC). The HPLC chromatogram is examined for the presence of a UV absorbing peak (at 210 nm) eluting at between about 6.4 minutes to about 6.7 minutes when using an Amino Carbohydrate column and an acetonitrile gradient as the solvent system. The chromatogram is then compared to one obtained from a control individual (i.e., a sample obtained from a patient having gross cystic disease and the same type of cyst fluid but without breast cancer). If the peak at 6.4 to 6.7 minutes present in the patients' cyst fluid is at least 50% larger than that of the control, the patient has an increased risk of developing breast cancer. The presence of this peak is correlated with the development of breast cancer in women with gross cystic disease.

Alternatively, the presence of a large peak (greater than two standard deviation above that obtained from control extracts from individuals who are cancer free) at 7.4 to 7.8 minutes when analyzed by HPLC as above, is at an increased risk for developing breast cancer.

Control breast cyst fluids (30 samples were used of Type 1 and Type 2 cyst fluids) used in practicing the present invention are obtained from cancer-free individuals and treated identically with the samples to be tested, i.e. the samples are extracted and fractionated by chromatography on HPLC. The fractions are analyzed spectrophotometrically for absorbance at 210 nm. The values obtained (in arbitrary units) are used as a reference value. The mean and standard deviation are calculated for the control. Any samples which contain a UV absorbing peak (at 210 nm) which has a retention time of 6.4 to 6.7 minutes which is at least 50% or larger than the peak height of the peak having a retention time of 7-8 minutes is indicative of an increased risk for breast cancer. Alternatively, any individual whose cyst fluid extract has a peak at 7.4 to 7.8 minutes retention time on HPLC which is greater than 2 standard deviations above the mean of the control group is also at increased risk for cancer.

Non-limiting examples of the organic solvent used to prepare the samples of cyst fluid extracts for HPLC include, methylene chloride, toluene, methanol, ethanol and preferably acetonitrile. The organic solvent is mixed with the cyst fluid at a concentration of between about 60% and 85% (final concentration of solvent) and preferably 80% in order to remove contaminating materials for HPLC analysis. This causes the precipitation of unwanted materials, especially proteins, which are removed by low speed centrifugation (about $2000 \times g$ for about 5 minutes at 4° C. to 24° C.).

Suitable High Pressure Liquid Chromatography columns for use in the present invention are those which bind carbohydrate and/or polysaccharide-containing materials such as an Amino-Carbohydrate column (commercially available from Alltech, Chicago, Ill.).

The minimal amount of cyst fluid which can be examined using this procedure is 0.01 ml. The usual amount of fluid present in a single human breast cyst is between about 0.05 ml and 50 ml. The fluid is extracted only once with the organic solvent and filtered so that it can be injected into an HPLC column. The unique factors which are diagnostically predictive of human breast cancer can then be isolated by HPLC. As it is believed that the factors of the present invention will be reactive with digoxin antibodies (see below), radioimmunoassay for digoxin or other methods as well may also be employed for detection of these unique factors. It is envisioned that the preferred method of detection of these factors will comprise specific assays using antibodies directed against the purified factors. This will allow for detection of these factors in crude isolates of breast cyst fluid (or serum), perhaps making the extraction and HPLC isolation steps unnecessary.

One factor, which is a diagnostic indicator of breast cancer, when it is present in amounts at least 50% of the peak at 7-8 minutes in control fluids (obtained from cancer-free individuals) is soluble in acetonitrile, absorbs light at 210 nm (indicative of carbonyl or $C=C$ bonds) and has a retention time on an Amino Carbonhydrate HPLC using a gradient of acetonitrile:water of between about 6.4 and 6.7 minutes. Although not 100% of the women studied who had an increase in this peak in their breast cyst fluid were subsequently diagnosed as having breast cancer (for example, 4 out of 7 with Type 1 fluids), it is possible that the cancer had not yet become apparent in these healthy women as this is a very early indicator of the disease. Therefore, these women should be very closely monitored as early detection and treatment of the cancer greatly increases the survival rate of patients with breast cancer. In addition, when detected during the early course of the disease, less invasive treatments can be employed and these are more effective.

The present inventors have also identified a similar factor as the 6.4 to 6.7 minute factor of the present invention in bovine adrenal extracts. The bovine material is soluble in acetonitrile, absorbs light at 210 nm and has a retention time of 6.4 minutes when using HPLC with an Amino Carbohydrate column and an acetonitrile gradient. Without wishing to be bound by theory, it is hypothesized that the diagnostic indicator of breast cancer may be produced by the adrenal glands and transported and concentrated within breast cysts. If this indeed is true, it may be possible to detect this factor not only in the serum of women with gross cystic disease, but also in the serum of those without gross cystic disease.

The present inventors believe that the factors which are diagnostic indicators of increased risk for breast cancer will also cross-react with antibodies directed against digoxin in specific radioimmunoassays (RIAs) for the cardiac glycoside. Such RIAs are commercially available from New England Nuclear (Boston, Mass.) Cat. No. A082) or Clinical Assays (Cambridge, Mass.) and are performed as in Example 2 below.

Therefore, the development of breast cancer in women with gross cystic disease seems to be correlated with differences in compounds related to digoxin-like materials. These characteristics may be used to identify a group of women at increased risk for developing breast cancer.

The present invention is further described below in working examples which are intended to illustrate the present invention without limiting its scope.

EXAMPLE 1

The present inventors studied HPLC extracts from 70 cyst fluid samples.

To obtain material for study, cyst fluid was isolated by fine needle aspiration from human females with gross cystic disease of the breast. The isolated fluid was frozen at $-20°$ C. before use. The fluids were thawed and the ionic concentration (i.e. the concentration of sodium, chloride and potassium) of each sample was determined using ion selective electrodes, with a Beckman E4a analyzer.

A summary of the electrolyte composition of the cyst fluid samples is presented below in Table I.

TABLE I

| | Electrolyte composition of cyst fluid samples | | | |
|---|---|---|---|---|
| | | Representative Electrolyte Characterization | | |
| Type | Number of Samples | $Na^+$ mM | $K^+$ mM | $Cl^-$ mM |
| 1 | 39 | <35 | >100 | <15 |
| 2 | 8 | >100 | <15 | >80 |
| A | 23 | Intermediate | | |

Cyst fluid (0.25 ml) was diluted with 0.75 ml of water, mixed with acetonitrile (4ml) and centrifuged at 2,000×g at 4° C. The supernatant was filtered with a nylon filter (Acro LC-25, 0.25 microns, Gelman Sciences, Ann Arbor, Mich.) in order to remove contaminating particulate material.

Aliquots of the filtrate (0.05 ml) were injected directly onto the HPLC (Model 400 Bio-Rad, Richmond, Calif.) via an 0.20 ml sample loop. The column used was an Amino Carbohydrate cartridge column (4.1×250 mm, Alltech, Chicago, Ill.) with a complex gradient using a mixture of acetonitrile and water as follows: (a) t=0 min., 95% acetonitrile; (b) t=2 min., 75% acetonitrile; (c) t=10 min., 55% acetonitrile; (d) t=12 min., 40% acetonitrile; (e) t=14 min., 95% acetonitrile. Materials were detected by UV absorbance at 210 nm.

Figure 4:
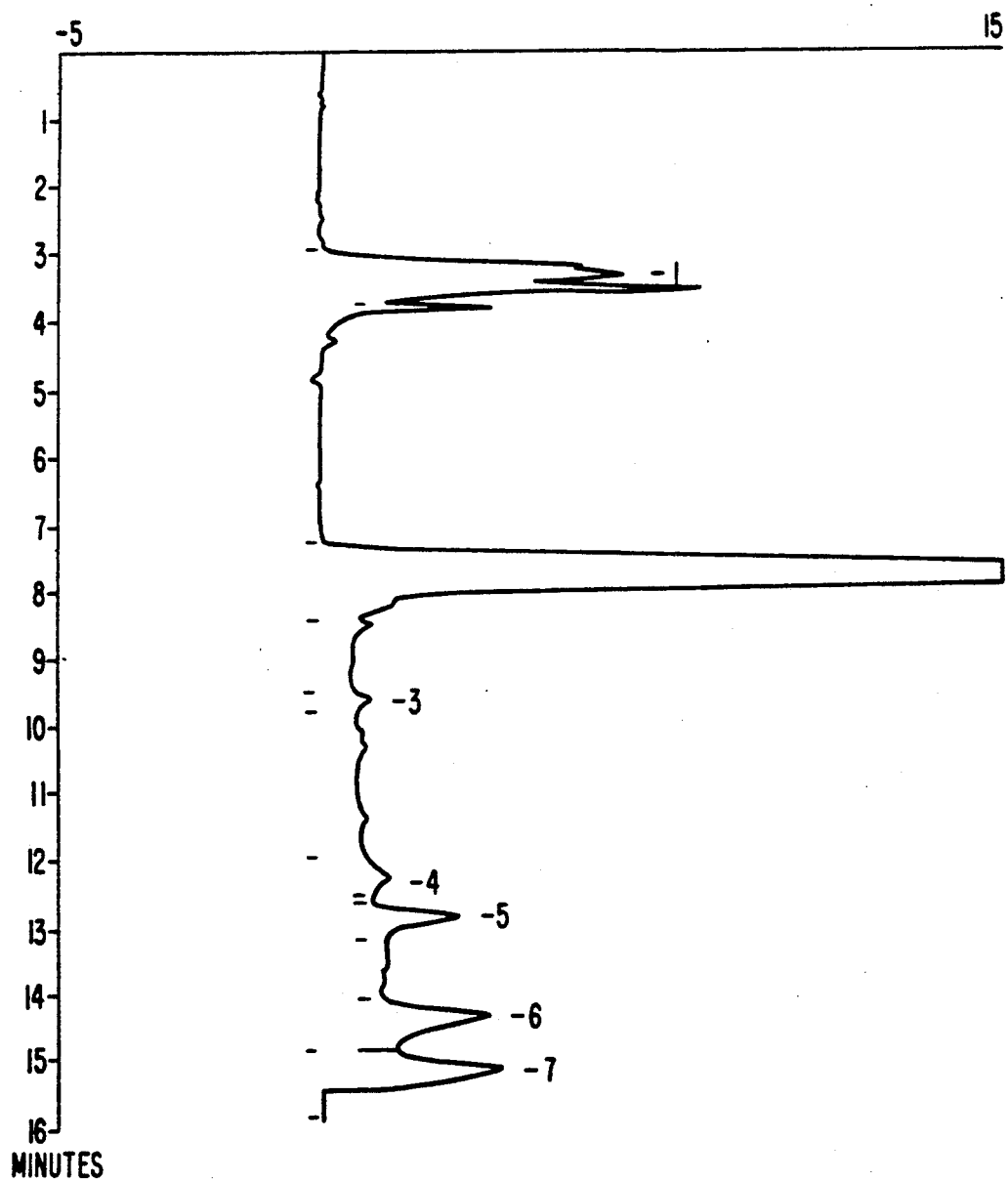
FIG. 4 is an HPLC chromatogram of an extract from Type 1 human breast cyst fluid from an individual with breast cancer.
Figure 5:
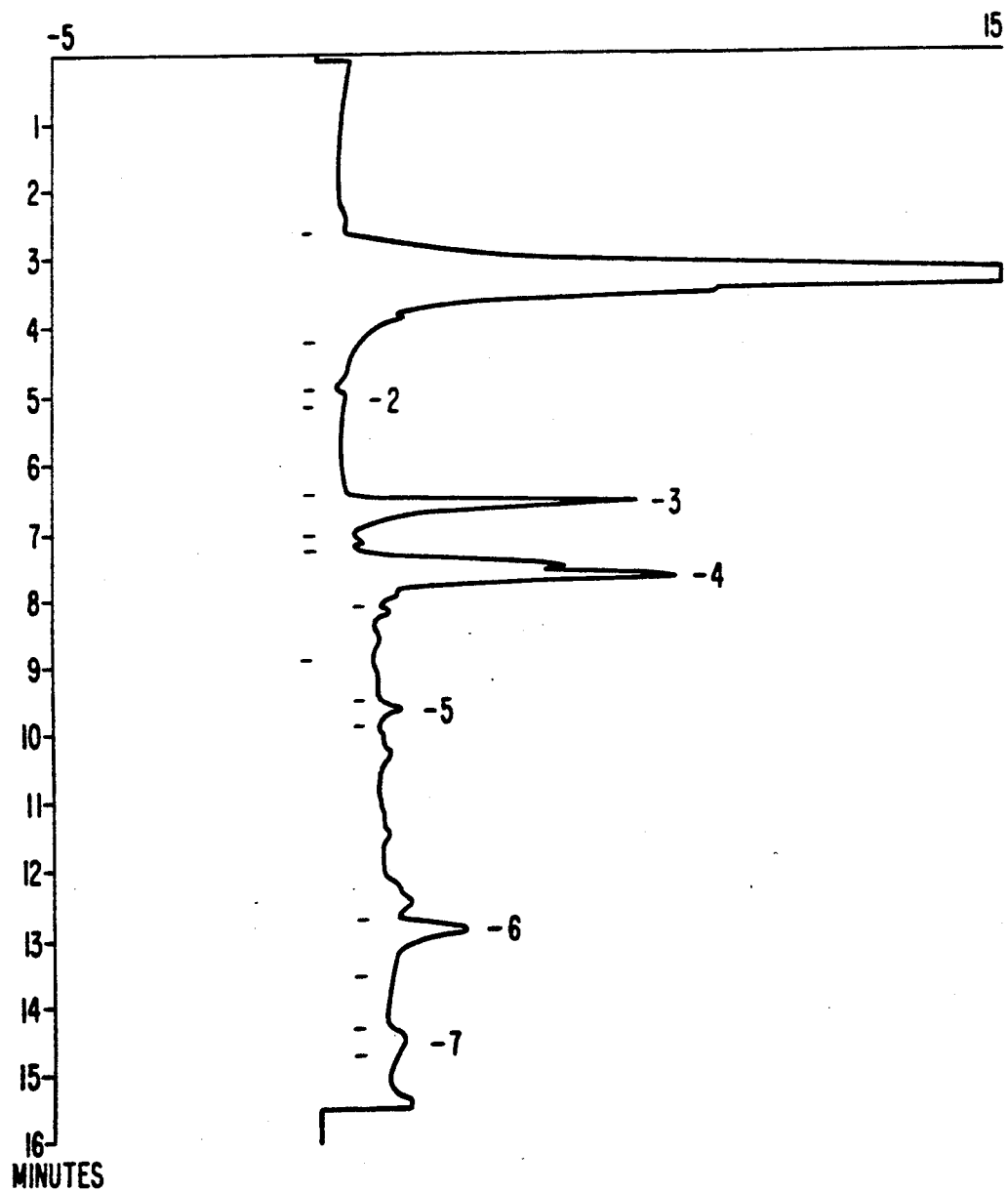
FIG. 5 is an HPLC chromatogram of an extract from Type 1 human breast cyst fluids with a peak at 6.5 minutes and breast cancer.

A representative chromatoqraph of normal Type 1 extracts is shown in FIG. 1. All of the 39 extracts from Type 1 cyst fluids had a major peak between 7.6 and 7.8 minutes after injection (FIG. 1). The peak (numbered no. 6 in FIG. 1) was not a single compound but it seemed to be a mixture with additional shoulders on both the leading and trailing sides. The mean peak height maximum was 10 with a standard deviation of three. In two of the extracts, the peak height was greater than three standard deviations above the mean (FIG. 4). Both women had breast cancer. Seven of the extracts had peaks at 6.4 to 6.7 minutes that were greater than half the height of the major peak, a representative chromatograph is shown in FIG. 5. Of these, not less than four had breast cancer. One woman had repeated cysts; the peak at 6.4 minutes was not present two years prior to the development of the cancer but was present within six months of the diagnosis.

Figure 2:
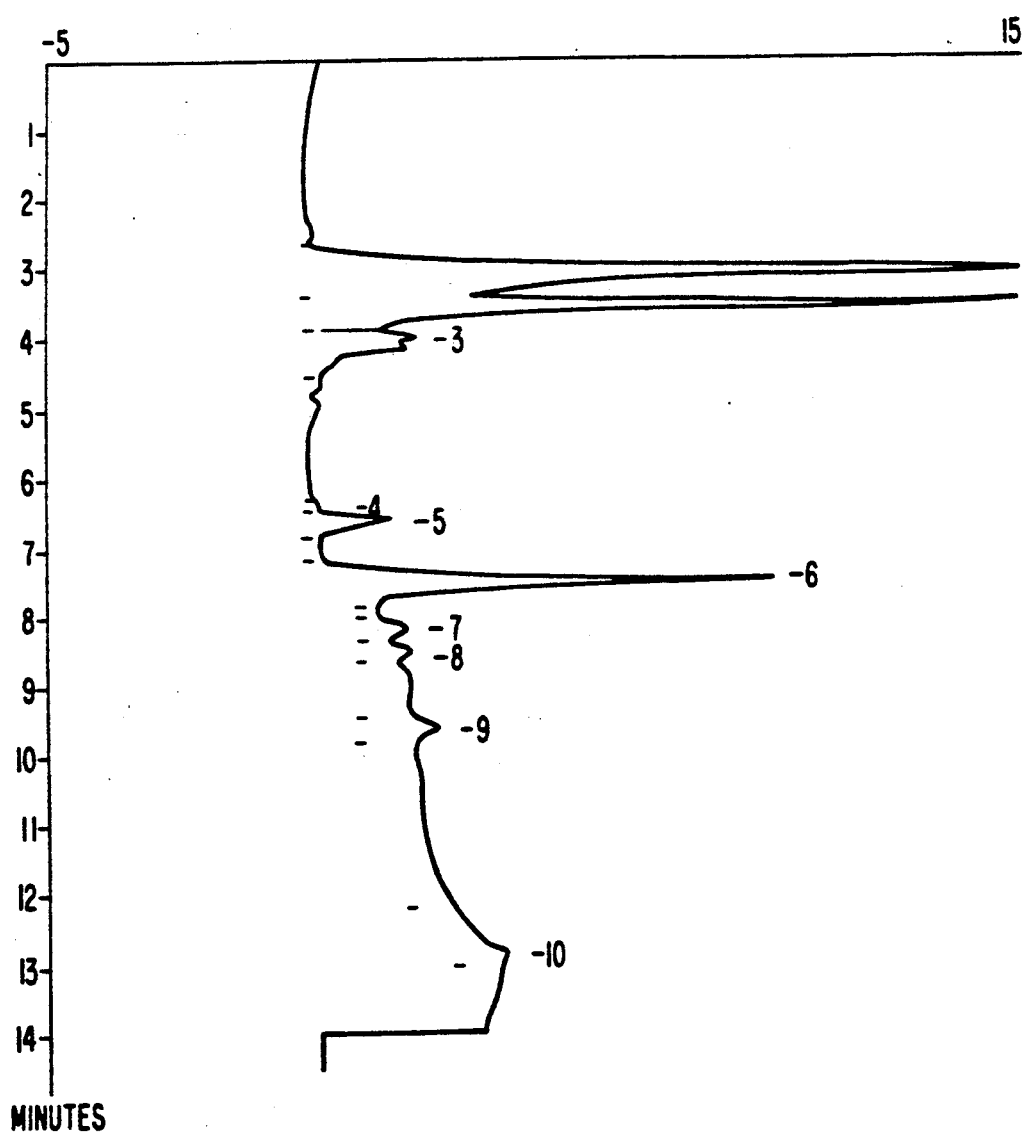
FIG. 2 is an HPLC chromatogram of an extract from Type 2 human breast cyst fluid from an individual without breast cancer.

The chromatograms from the Type 2 cyst extracts were significantly different from the Type 1 extracts. The major central peak was at 7.5 to 7.7 minutes (number 6 in FIG. 2) and was smaller. The peak had no shoulders and overlapped in retention time the corresponding peak in Type 1 extracts. One sample had a large peak at 6.5 minutes and this woman developed breast cancer.

Figure 3:
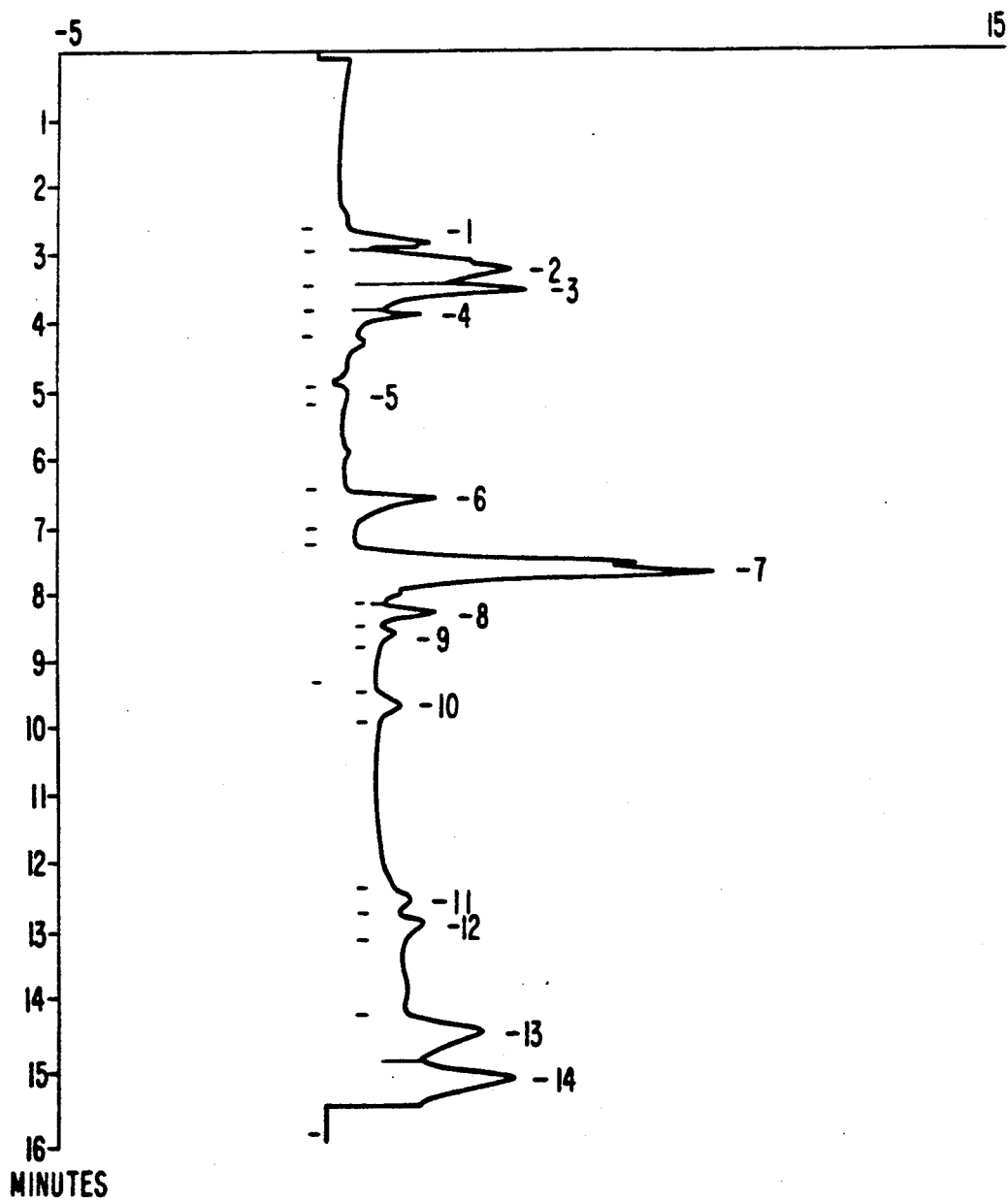
FIG. 3 is an HPLC chromatogram of an extract from Type A human breast cyst fluid without breast cancer.
Figure 6:
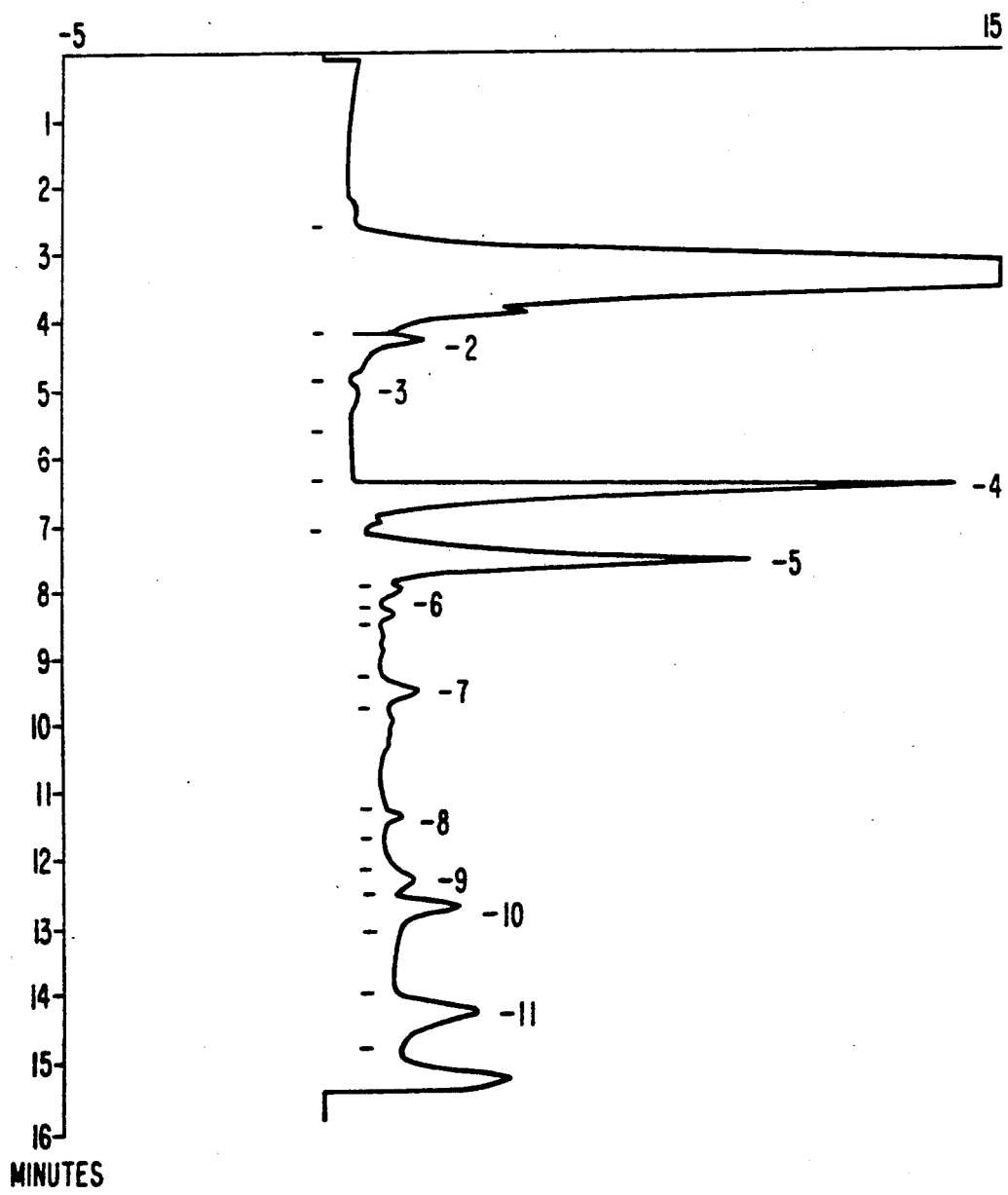
FIG. 6 is an HPLC chromatogram of an extract from Type A human breast cyst fluids with a peak at 6.5 minutes and breast cancer.

The chromatograms from extracts of the cyst fluids with Type A electrolyte pattern (FIG. 3) were similar to the extracts from the Type 1 fluids. There was a tendency for the central peak to be smaller but there were several shoulders as was noted in the Type 1 extracts. Two of the samples also had major peaks at 6.5 minutes. At least one of these women was subsequently diagnosed as having breast cancer (FIG. 6).

EXAMPLE 2

The factors of the present invention will be assayed for their ability to cross-react with antibodies directed against digoxin as follows. Human breast cyst fluid (from a patient having gross cystic disease and with a positive diagnosis of breast cancer) will be extracted and chromatographed on HPLC as described in Example 1 above. The material eluting at between 6.4 and 6.7 minutes and 7.6 and 7.8 minutes will be recovered, placed in a 12×75 mm culture tubes and the solvents removed by evaporation under a stream of nitrogen gas.

The standard digoxin assay as recommended by the manufacturer will be modified in order to improve its sensitivity by (a) using 0.2 ml of both the tracer and antibody preparations instead of 0.5 ml and (b) extending the range of standards by 10-fold dilutions (using digoxin-free serum as the diluent) of the supplied standards to 5, 10 and 20 pg/tube. With these modifications, the assay can detect as little as 5 pg/tube.

0.2 ml of [$^{125}$I]-labeled digoxin tracer and 0.2 ml of digoxin antibody are added to each tube containing the dried samples from the Amino Carbohydrate column. The standard solutions mentioned above are evaporated and treated identically. The tubes are mixed by vortex and allowed to incubate for 45 minutes at room temperature. Thereafter, the tubes are centrifuged at 2000×g at 4° C. for 30 minutes and transferred to foam decanting racks (Diagnostic Products, Los Angeles, Calif.) and decanted. Each tube is blotted and the amount of [$^{125}$I] is determined using a gamma counter (Model 1275 Mini-Gamma, LKB, Gaithersburg, Md.). Individual values of digoxin are determined by interpolation against a standard curve obtained at the same time using a smooth spline best fit program from LKB and are expressed as ng or pg digoxin equivalents.

The present invention has been described above in reference to preferred embodiments. It would be apparent to those skilled in the art that many additions, deletions and substitutions could be made without departing from the spirit and scope of the invention as claimed below.

What is claimed is:

1. A method for determining whether a patient with breast cyst disease is at an increased risk of developing breast cancer comprising the steps of:

collecting an unknown sample of breast cyst fluid from a patient in question of developing breast cancer and a control sample of breast cyst fluid from an individual with breast cyst disease but free of breast cancer, extracting said unknown and control samples with an organic solvent to created an extracted unknown and control sample, applying each of said extracted samples to an Amino-Carbohydrate column and isolating a unknown fraction and a control fraction each having retention times on the column of between about 6.4 and 6.7 minutes, examining each of said fractions for a 210 nm absorbing materials, comparing the amount of 210 nm absorbing material in the unknown fraction to the amount of 210 nm absorbing material in the control fraction, wherein said patient is at an increased risk of developing breast cancer if the amount of 210 nm absorbing material in the unknown fraction is 50 percent or greater than the 210 nm absorbing material in the control fraction.

2. A method for identifying a patient having gross breast cystic disease who has an increased risk for developing breast cancer comprising the steps of:

collecting a sample of breast cyst fluid from a patient in question of developing breast cancer, extracting said sample with acetonitrile to created a extracted sample, applying said extracted sample to an Amino-Carbohydrate column with an acetonitrile gradient as the solvent and isolating a first fraction having a retention time on the column of between about 6.4 and 6.7 minutes and a second fraction with a retention between about 7 and 8 minutes, examining said first and second fractions for 210 nm absorbing material, comparing the amount of 210 nm absorbing material in the first fraction to the amount of 210 nm absorbing material in the second fraction, wherein said patient is at an increased risk of developing breast cancer if the amount of 210 nm absorbing material in the first fraction is 50 percent or greater than the 210 nm absorbing material in the second fraction.

3. A diagnostic system for determining if a female patient with breast cyst disease is at increased risk of developing carcinoma of the breast which comprises:

collecting a sample of breast cyst fluid from a female patient in question of developing breast cancer, extracting said sample with an organic solvent to created an extracted sample, applying said extracted sample to an Amino-Carbohydrate column and isolating a first fraction having a retention time on the column of between about 6.4 and 6.7 minutes and a second fraction having a retention time of between about 7 and 8 minutes, examining each of said fractions for a 210 nm absorbing material, examining said first and second fractions for 210 nm absorbing material, comparing the amount of 210 nm absorbing material in the first fraction to the amount of 210 nm absorbing material in the second fraction, wherein said patient is at an increased risk of developing breast cancer if the amount of 210 nm absorbing material in the first fraction is 50 percent or greater than the 210 nm absorbing material in the second fraction.

4. A method for determining whether a patient with breast cyst disease is at an increased risk for developing breast cancer comprising the steps of:

collecting an unknown sample of breast cyst fluid from a patient in question of developing breast cancer and a control sample of breast cyst fluid from an individual with breast cyst disease but free of breast cancer, extracting said unknown and control samples with an organic solvent to created an extracted unknown and control sample, applying each of extracted samples to an Amino-Carbohydrate column and isolating a first fraction and a control fraction having retention times on the column of between about 7.4 and 7.8 minutes, examining each of said fractions for 210 nm absorbing material, comparing the amount of 210 nm absorbing material in the unknown fraction to the amount of 210 nm absorbing material in the control fraction, wherein said patient is at an increased risk of developing breast cancer if the amount of 210 nm absorbing material in the unknown fraction is about two standard deviations greater than the mean amount of the 210 nm absorbing material in the control fraction.

5. A method for determining whether a patient with breast cyst disease is at an increased risk of developing breast cancer comprising the steps of:

collecting a unknown sample of breast cyst fluid from a patient in question of developing breast cancer and a control sample of breast cyst fluid from an individual with breast cyst disease but free of breast cancer, extracting said unknown and control samples with an organic solvent to created an extracted unknown and control sample, applying each of said extracted samples to an Amino-Carbohydrate column and isolating a first unknown fraction and a first control fraction each having retention times on the column of between about 6.4 and 6.7 minutes and a second unknown fraction and a second control fraction having a retention time of between about 7.4 and about 7.8 minutes, examining each of said fractions for a 210 nm absorbing material, comparing the amount of 210 nm absorbing material in the unknown fraction to the amount of 210 nm absorbing material in the control fraction, wherein said patient is at an increased risk of developing breast cancer if the amount of 210 nm absorbing material in the first unknown fraction is 50 percent or greater than the 210 nm absorbing material in the first control fraction or said patient is at an increased risk of developing breast cancer if the amount of 210 nm absorbing material in the second unknown fraction is about two standard deviations greater than the mean amount of the 210 nm absorbing material in the second control fraction.

6. A method for determining whether a patient with breast cyst disease is at an increased risk of developing breast cancer comprising the steps of:

collecting a unknown sample of breast cyst fluid from a patient in question of developing breast cancer and a control sample of breast cyst fluid from an individual with breast cyst disease but free of breast cancer, extracting said unknown and control samples with acetonitrile to created an extracted first and control sample, applying each of said extracted samples to an Amino-Carbohydrate column with an acetonitrile gradient as the solvent and isolating a first unknown fraction and a first control fraction each having retention times on the column of between about 6.4 and 6.7 minutes and a second unknown fraction and a second control fraction having a retention time of between about 7.4 and about 7.8 minutes, examining each of said fractions for a 210 nm absorbing material, comparing the amount of 210 nm absorbing material in the unknown fraction to the amount of 210 nm absorbing material in the control fraction, wherein said patient is at an increased risk of developing breast cancer if the amount of 210 nm absorbing material in the first unknown fraction is 50 percent or greater than the 210 nm absorbing material in the first control fraction or said patient is at an increased risk of developing breast cancer if the amount of 210 nm absorbing material in the second unknown fraction is about two standard deviations greater than the means amount of the 210 nm absorbing material in the second control fraction.

* * * * *